US00PP12343P2

(12) United States Plant Patent
Saul

(10) Patent No.: US PP12,343 P2
(45) Date of Patent: Jan. 8, 2002

(54) *KNIPHOFIA UVARIA* PLANT NAMED 'CANDLE LIGHT'

(76) Inventor: Richard Gregg Saul, 308 Hester Valley Rd., Cleveland, GA (US) 30528

( * ) Notice: Subject to any disclaimer, the term of this patent is extended or adjusted under 35 U.S.C. 154(b) by 0 days.

(21) Appl. No.: 09/710,807

(22) Filed: Nov. 13, 2000

(51) Int. Cl.[7] ..... A01H 5/00
(52) U.S. Cl. ..... Plt./263
(58) Field of Search ..... Plt./263, 373, 226

(56) References Cited

U.S. PATENT DOCUMENTS

P.P. 562 * 8/1942 Grullemans ..... Plt./263

* cited by examiner

*Primary Examiner*—Bruce R. Campell
*Assistant Examiner*—W C Baker

(57) ABSTRACT

A new and distinct variety of Kniphofia plant named 'Candle Light', characterized by its unique blooming period, bloom color, bloom form, and compact growth habit.

1 Drawing Sheet

BACKGROUND OF THE INVENTION

This new Kniphofia variety was found as an openly pollinated seedling of *Kniphofia uvaria* maintained in Dahlonega, Ga. The seedling, hereinafter referred to as 'Candle Light', was discovered by Richard Gregg Saul in June, 1996. The value of this new cultivar lies in its unique blooming period, bloom color, bloom form, and compact growth habit.

Asexual propagation of the new plant by division has been under Mr. Saul's direction at the same location. Several generations of the new plant have been evaluated and the distinctive characteristics of the plant have remained stable. The plant cannot be reproduced true from seed.

SUMMARY OF THE INVENTION

The following are the most outstanding and distinguishing characteristics of this new cultivar when grown under normal horticultural practices in Dahlonega, Ga.

1. The unique spring, summer, and fall blooming.
2. Attractive cream colored flowers held above the foliage on spike-like racemes.
3. Numerous flowers per plant.
4. Dense clumps of grasslike foliage.
5. Low, compact growth habit.
6. Easily propagated by division.
7. Heat and drought resistant.
8. Tolerates full sun to light shade.
9. Desirable in planters.
10. Desirable as a cut flower.
11. Effectively used in mass in perennial gardens.

12. Hardy to Zone 6.
13. Attracts hummingbirds and butterflies.

DESCRIPTION OF THE DRAWINGS

This new variety of *Kniphofia uvaria* is illustrated by the accompanying photograhic prints in which.

1.

2.

Figure 1:
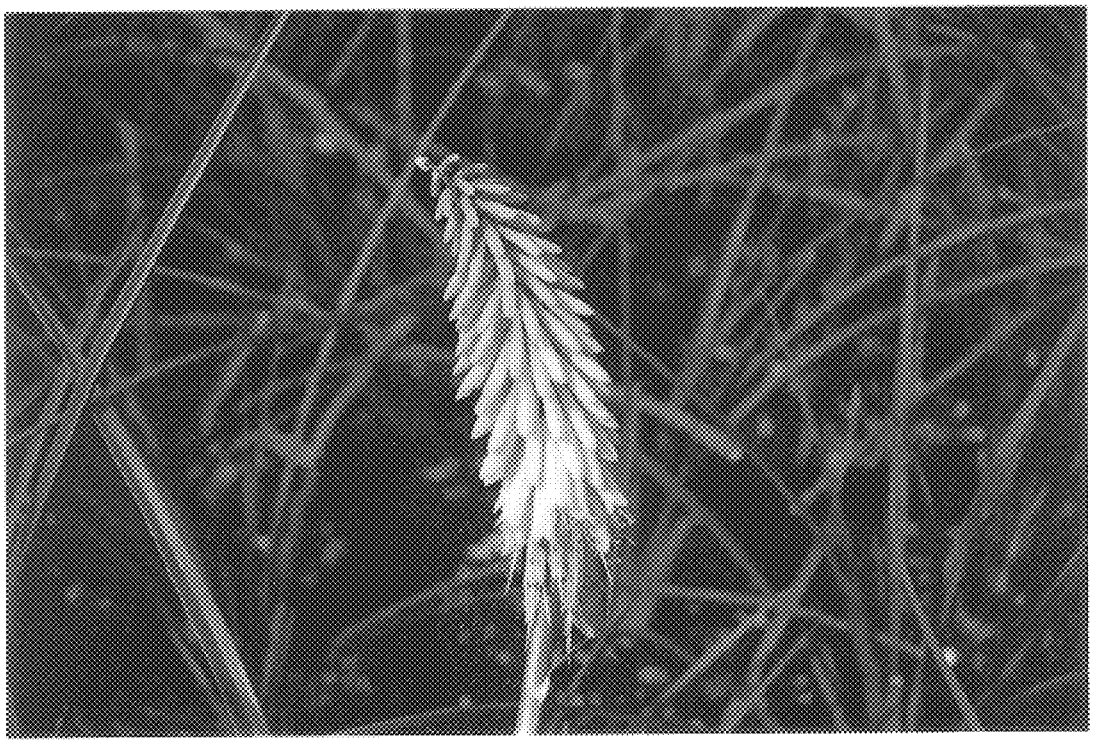
FIG. 1 is a close-up showing flower, foliage, and stem color as well as flower size and form.
Figure 2:
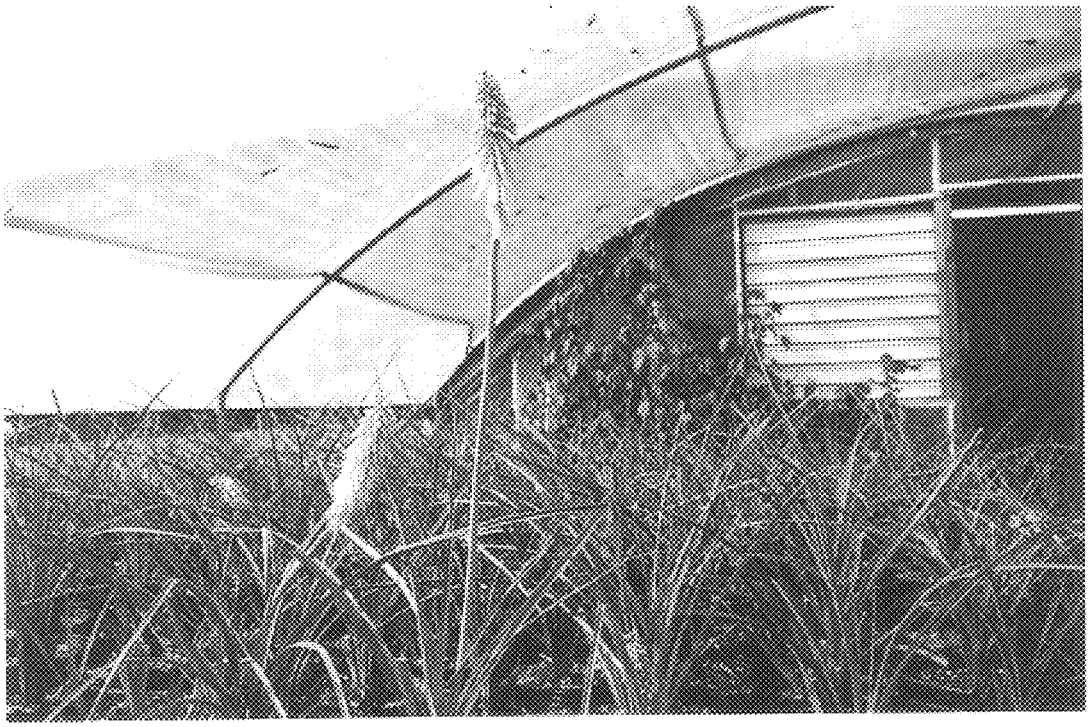
FIG. 2 shows the grasslike foliage of young three gallon plants, with multiple inflorescences.

The colors shown are as true as is reasonably possible to obtain by conventional photographic procedures. Colors in the photographs may appear different than actual colors due to light reflectance. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of an approximately two-year old plant of the new variety of Kniphofia based on my observations of plants grown in wholesale commercial production practices, in greenhouses, and in established landscape plantings in Dahlonega, Ga. The wholesale commercial production and established landscape plants were grown under ambient conditions at the location of culture with standard overhead irrigation; the greenhouse grown plants were kept in winter temperatures of 62 degrees Fahrenheit night and 85 degrees Fahrenheit day, summer temperatures of 65 degrees Fahrenheit night and 95 degrees Fahrenheit day, with no added light source and were hand-watered as needed.

Distinctive Characteristics:

| Characteristic | Kniphofia u. 'Candle Light' | Kniphofia u. 'Primrose Beauty' | Kniphofia u. (The Species) |
|---|---|---|---|
| Height (Mature) | 16–18" | 24–36" | 24–36" |
| Width (Mature) | 24–30" | 24–36" | 24–36" |

-continued

| Distinctive Characteristics: | | | |
|---|---|---|---|
| Characteristic | Kniphofia u. 'Candle Light' | Kniphofia u. 'Primrose Beauty' | Kniphofia u. (The Species) |
| Bloom Period | April to October | June to July | May to June |
| Bloom Height | 15–30" | 36–48" | 36–48" |
| Inflorescence Length | 5–6" | 6–10" | 6–10" |
| Inflorescence Width | 1½–2" | 2½–3" | 2½–3" |
| Flower Color | Creamy Yellow–White | Light Yellow | Red–Orange |
| Leaf Length | 12–16" | 24–36" | 24–36" |
| Leaf Width | ½–¾" | ½–1 ¼" | ½–1 ¼" |

Kniphofia 'Candle Light' can be compared to the non-patented plant Kniphofia 'Primrose Beauty' and the species *Kniphofia uvaria,* however, in side-by-side comparisons conducted in Dahlonega, Ga., there are many differences. As indicated above, 'Candle Light' has a more compact growth habit, longer blooming period, smaller inflorescence, and different bloom color.

Classification:

*Botanic.*—*Kniphofia uvaria* 'Candle Light'.

*Commercial.*—Herbaceous perennial.

*Form.*—Dense, grasslike clump.

*Height.*—Foliage 16 to 18". Blooms 15 to 30".

*Width.*—24 to 30".

*Size.*—In a period of two to three months from a division, the plant reaches a saleable size of 10 to 12" in a 3 quart container. Blooms begin to appear at this time and are held above the foliage at about 15".

*Foliage.*—Basal, semi-evergreen, grasslike, erect to slightly arching, rhizomatous, linear-ensiform, strongly keeled, margins rough, sharply pointed, and varying in size from 16 to 18" long and ½ to ¾" wide. Leaves are numerous and leaf veination is parallel. Immature leaves are Yellow-Green Group 144A top and bottom, dull and glabrous. Mature leaves are Green Group 138A top and bottom and also dull and glabrous. The base of the leaves is White Group 155A.

Like the parent species, 'Candle Light' has no above ground stems. It grows by adding bibs or small clumps of leaves on short rhizomes on the side of the existing clump. The rhizomes are normally less than one inch long. As the plant grows, the clump becomes larger, and can be propagated by separating the bibs. The root system is thick and cordlike.

In 1998, the date of initial spring growth was March 28, in Dahlonega, Ga. After the initial spring flush there was almost continuous growth until fall ending October 10, also in Dahlonega, Ga. This growth pattern was identical to the parent species, however, 'Candle Light' has a more compact growth habit than the parent species.

Flowers: Perfect, non-fragrant, drooping, on short, articulate pedicels, borne distally on 15 to 30" long indeterminate racemes. The pedicel is ⅛ to 3⁄16" long and Yellow-Green Group 144B. The racemes are Yellow-Green Group 144B and have a ¼ to ½" diameter at the base. The distal immature buds are ¼ to ½" long and Yellow-Green Group 150C. Maturing buds ½ to ¾" long are Yellow Group 5D. Flowers are ¾ to 1½" long, 3⁄16 to ¼" wide, and White Group 155A as they open. This collection of overlapping buds and opening flowers are 5 to 6" long and 1½ to 2" wide. The perianth is cylindrical to funnelform and has 6 lobes which are 1⁄16 to ⅛" long with acute tips. The 6 unequally exserted stamens are ¾ to 1⅛" long and the filaments are White Group 155A. The pollen is Yellow-Green Group 7B and the versatile anthers are Greyed-Orange Group 165A at maturity. The pistil is single, 1 to 1¼" long, and Yellow-Green Group 149D. The ovary is ⅛ to 3⁄16" long, 1⁄16 to ⅛" wide and Yellow-Green Group 145A. Nectar-bearing glands are located at the base of each flower and produce an abundant amount of nectar.

Flowering normally begins in April and continues through fall. A very attractive inflorescence results from the maturation of creamy yellow buds to pure white flowers. Individual flowers last on the plant about 7 days and the inflorescence continues to bloom for about 14 to 21 days. As cut flowers, an inflorescence will last 7 to 14 days. A mature plant will produce from 90 to 175 blooms per raceme and 20 to 25 racemes per plant.

Fruit: Loculicidally three-valved capsule, ⅛ to ¼" long, 1⁄16 to ⅛" wide, and Yellow-Green Group 144A at maturity. Seeds are many, fertile, flat, and in two rows in each cell. Few capsules are produced.

Culture: Grows well in a wide range of conditions and tolerates sun to light shade. Grows in nearly any soil type, from moist to dry and sand to clay. Very heavy clays should be amended with peat moss, compost, or shredded pine bark to improve the soil texture. Poorly drained locations should be avoided. Responds well to mulching and medium applications of fertilizer; prefers ph 6 to 7. Propagated by division in the spring.

Disease/pest resistance: Plants of the new variety, to date, do not appear to be more or less resistant to disease and pests than those of the species in general.

I claim:

1. A new and distinct variety of Kniphofia plant named 'Candle Light', as described and illustrated.

* * * * *